United States Patent [19]

Jenkins

[11] Patent Number: 4,659,762

[45] Date of Patent: Apr. 21, 1987

[54] TRIS (SUBSTITUTED HYDROXYPHENYLTHIO) TRITHIOORTHOESTER STABILIZERS FOR POLYMERS

[75] Inventor: Linda A. Jenkins, Palisades Park, N.J.

[73] Assignee: Ciba-Geigy Corporation, Ardsley, N.Y.

[21] Appl. No.: 889,044

[22] Filed: Jul. 25, 1986

[51] Int. Cl.[4] .................. C08K 5/36; C07C 149/36; C10M 135/30

[52] U.S. Cl. ................... 524/331; 252/48.2; 568/47

[58] Field of Search ............... 568/47, 592; 524/331, 524/326; 252/48.2

[56] References Cited

U.S. PATENT DOCUMENTS

| | | | |
|---|---|---|---|
| 2,564,795 | 8/1951 | Sibley | 524/388 |
| 2,677,708 | 5/1954 | Copenhaver | 524/339 |
| 3,525,710 | 8/1970 | Wood | 524/368 |
| 3,576,883 | 4/1971 | Neuworth | 568/47 |
| 3,683,032 | 8/1972 | Braid | 568/592 |
| 3,704,327 | 11/1972 | Neuworth | 568/47 |
| 4,134,879 | 1/1979 | Schmidt | 568/592 |
| 4,611,023 | 9/1986 | Spivak et al. | 524/331 |

OTHER PUBLICATIONS

Seebach et al: Chem. Ber. 105, 3280–3300, (1972).
DeWolfe, R. H.: *Organic Chemistry* vol. 14: Carboxylic Ortho Acid Derivatives, 269–271 and 349–419 (1970), Academic Press, Inc. N.Y., N.Y.

*Primary Examiner*—Veronica Hoke
*Attorney, Agent, or Firm*—Harry Falber

[57] ABSTRACT

The title compounds correspond to the formula

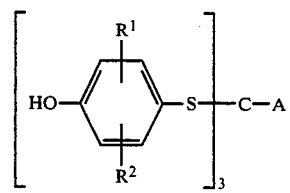

and are useful as stabilizers for organic polymers and lubricating oils to counteract the degradative effects of heat, light and air.

14 Claims, No Drawings

TRIS (SUBSTITUTED HYDROXYPHENYLTHIO) TRITHIOORTHOESTER STABILIZERS FOR POLYMERS

Organic polymeric materials such as plastics and resins, and lubricating and mineral oils are subject to thermal, oxidative and photo-degradation. A wide variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

It has now been determined that the trithioorthoester derivatives of this invention possess an unusual combination of desirable properties which makes them particularly effective and useful as stabilizers. The compounds are particularly effective in protecting polyolefins, high impact polystyrene, rubbers such as polybutadiene and styrene-butadiene rubber, and other elastomers wherein retention of elasticity and inhibition of cross-linking, crazing, discoloration, odor formation and exudation are basic requirements.

Various trithioorthoesters are known in the art, these derivatives generally being disclosed as reactants for the synthesis of other organic compounds. For example, tris(phenylthio) alkanes, hydroxy-substituted alkanes, hydroxy-substituted aralkanes, alkyl esters, and various salts thereof have been disclosed in the March, 1986 Fluka Chemical Catalog; in Seebach, Chem. Ber., 105, 487–510 (1972); in Cohen et al, J. Am. Chem. Soc., 105, 2811–2813 (1983); and in Makosza et al, Chemistry Letters, pp 1623–24 (1984). In addition, tri-para(halo, alkyl, methoxy, amino, nitro)phenyl trithioorthomethanes have been disclosed in Jeminet et al, Bull. Soc. Chim. Fr., 9, 3233–43 (1967); in Seebach et al, Chem. Ber., 105, 3280–3300 (1972); and in Gowery, J. Chem. Soc. Chem. Commun., 16, 634 (1984). As noted, these structurally distinct compounds are disclosed solely as tools for organic synthesis.

It is the primary object of this invention to provide a class of trithioorthoester derivatives which exhibit a broad range of improved stabilization performance characteristics.

Various other objects and advantages of this invention will become evident from the following description thereof.

The compounds of this invention correspond to the formula

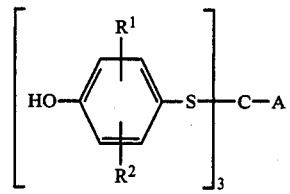

wherein $R^1$ and $R^2$ are independently hydrogen, alkyl of 1 to 18 carbon atoms, cycloalkyl of 5 to 12 carbon atoms, phenyl, phenyl substituted by alkyl of 1 to 18 carbon atoms, aralkyl of 7 to 9 carbon atoms or said aralkyl substituted by alkyl of 1 to 18 carbon atoms; and A is hydrogen, alkyl of 1 to 30 carbon atoms, cycloalkyl of 5 to 12 carbon atoms, aryl, aryl substituted by alkyl of 1 to 18 carbon atoms, aralkyl of 7 to 9 carbon atoms or said aralkyl substituted by alkyl of 1 to 12 carbon atoms.

Preferred compounds within the above structure are those wherein both $R^1$ and $R^2$ are in the ortho position to the hydroxy group. The $R^1$ and $R^2$ groups are preferably straight-chain or branched alkyl with 1 to 8 carbon atoms, such as methyl, n-butyl, sec-butyl, tert-butyl, tert-pentyl 2-ethylhexyl, n-octyl and 1,1,3,3-tetramethylbutyl. The groups methyl, tert-butyl, tert-pentyl and 1,1,3,3-tetramethylbutyl are especially preferred. Also especially preferred, as previously noted, is for the $R^2$ group to be in the ortho position to the hydroxy group, particularly if $R^2$ is tert-alkyl.

When $R^1$, $R^2$ or A is aralkyl, it represents benzyl, alpha-methylbenzyl or alpha, alpha-dimethylbenzyl. Aryl substituents are generally derived from phenyl, tolyl, mesityl, xylyl and 1- and 2-naphthyl.

A is preferably hydrogen, alkyl of 1 to 18 carbon atoms or phenyl.

The compounds of this invention can be prepared by reacting the appropriate mercaptophenol with the appropriate trialkylorthoester [(alk)₃C-A] (to provide-C-A group) in an acidic reaction system. The reaction is generally not conducted in the presence of a solvent, although aromatic solvents such as benzene, toluene, xylene, and the like, aliphatic solvents such as heptane, or alcohols such as ethanol, may be present. The reaction temperature generally ranges from 25° to 80° C. The starting materials utilized to prepare these compounds are items of commerce or can be prepared by known methods.

Compounds of this invention are particularly effective in stabilizing organic materials such as plastics, polymers and resins in addition to mineral and synthetic fluids such as lubricating oils, circulating oils, etc.

Substrates in which the compounds of this invention, are particularly useful are polyolefins such as polyethylene and polypropylene; polystyrene, including impact polystyrene, ABS resin, SBR, isoprene, as well as natural rubber, polyesters including polyethylene terephthalate and polybutylene terephthalate, including copolymers, and lubricating oils such as those derived from mineral oil.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example,
  2,6-di-tert.butyl-4-methylphenol
  2-tert.butyl-4,6-dimethylphenol
  2,6-di-tert.butyl-4-ethylphenol
  2,6-di-tert.butyl-4-n-butylphenol
  2,6-di-tert.butyl-4-i-butylphenol
  2,6-di-cyclopentyl-4-methylphenol
  2-(α-methylcyclohexyl)-4,6-dimethylphenol
  2,6-di-octadecyl-4-methylphenol
  2,4,6-tri-cyclohexylphenol
  2,6-di-tert.butyl-4-methoxymethylphenol 1.2. Alkylated hydroquinones, for example,
  2,6-di-tert.butyl-4-methoxyphenol
  2,5-di-tert.butyl-hydroquinone
  2,5-di-tert.amyl-hydroquinone
  2,6-diphenyl-4-octadecyloxyphenol 1.3. Hydroxylated thiodiphenyl ethers, for example
  2,2'-thio-bis-(6-tert.butyl-4-methylphenol)
  2,2'-thio-bis-(4-octylphenol)
  4,4'-thio-bis-(6-tert.butyl-3-methylphenol)
  4,4'-thio-bis-(6-tert.butyl-2-methylphenol)

1.4. Alkylidene-bishenols, for example,
  2,2'-methylene-bis-(6-tert.butyl-4-methylphenol)
  2,2'-methylene-bis-(6-tert.butyl-4-ethylphenol)
  2,2'-methylene-bis-[4-methyl-6-(α-methylcyclohexyl)-phenol]
  2,2'-methylene-bis-(4-methyl-6-cyclohexylphenol)
  2,2'-methylene-bis-(6-nonyl-4-methylphenol)
  2,2'-methylene-bis-[6-(α-methylbenzyl)-4-nonylphenol]
  2,2'-methylene-bis-[6-(α,α-dimethylbenzyl)-4-nonylphenol]
  2,2'-methylene-bis-(4,6-di-tert.butylphenol)
  2,2'-ethylidene-bis-(4,6-di-tert.butylphenol)
  2,2'-ethylidene-bis-(6-tert.butyl-4-isobutylphenol)
  4,4'-methylene-bis-(2,6-di-tert.butylphenol)
  4,4'-methylene-bis-(6-tert.butyl-2-methylphenol)
  1,1-bis-(5-tert.butyl-4-hydroxy-2-methylphenyl-butane
  2,6-di-(3-tert.butyl-5-methyl-2-hydroxybenzyl)-4-methylphenol
  1,1,3-tris-(5-tert.butyl-4-hydroxy-2-methylphenyl)-butane
  1,1-bis-(5-tert.butyl-4-hydroxy-2-methylphenyl)-3-n-dodecylmercaptobutane
  ethylenglycol-bis-[3,3-bis-(3'-tert.butyl-4'-hydroxyphenyl)-butyrate]
  di-(3-tert.butyl-4-hydroxy-5-methylphenyl)-dicyclopentadiene
  di-[2-(3'-tert.butyl-2'-hydroxy-5'-methyl-benzyl)-6-tert.butyl-4-methylphenyl]-terephthalate.

1.5. Benzyl compounds, for example,
  1,3,5-tri-(3,5-di-tert.butyl-4-hydroxybenzyl)-2,4,6-trimethylbenzene
  di-(3,5-di-tert.butyl-4-hydroxybenzyl)-sulfide
  3,5-di-tert.butyl-4-hydroxybenzyl-mercapto-acetic acid isooctyl ester
  bis-(4-tert.butyl-3-hydroxy-2,6-dimethylbenzyl)dithiol-terephthalate
  1,3,5-tris-(3,5-di-tert.butyl-4-hydroxybenzyl)-isocyanurate
  1,3,5-tris-(4-tert.butyl-3-hydroxy-2,6-dimethylbenzyl)isocyanurate
  3,5-di-tert.butyl-4-hydroxybenzyl-phosphoric acid-dioctadecyl ester
  3,5-di-tert.butyl-4-hydroxybenzyl-phosphoric acid-monoethyl ester, calcium-salt 1.6. Acylaminophenols, for example,
  4-hydroxy-lauric acid anilide
  4-hydroxy-stearic acid anilide
  2,4-bis-octylmercapto-6-(3,5-tert.butyl-4-hydroxyanilino)-s-triazine
  octyl-N-(3,5-di-tert.butyl-4-hydroxyphenyl)-carbamate 1.7. Esters of β-(3,5-di-tert-butyl-4-hydroxyphenyl)-propionic acid with monohydric or polyhydric alcohols, for example,
  methanol
  octadecanol
  1,6-hexanediol
  neopentylglycol
  thiodiethyleneglycol
  diethyleneglycol
  triethyleneglycol
  pentaerythritol
  tris-hydroxyethyl isocyanurate
  di-hydroxyethyl oxalic acid diamide 1.8. Esters of β-(5-tert-butyl-4-hydroxy-3-methylphenyl)propionic acid with monohydric or polyhydric alcohols, for example,
  methanol
  octadecanol
  1,6-hexanediol
  neopentylglycol
  thiodiethyleneglycol
  diethyleneglycol
  triethyleneglycol
  pentaerythritol
  tris-hydroxyethyl isocyanurate
  di-hydroxyethyl oxalic acid diamide 1.9. Amides of β-(3,5-di-tert.butyl-4-hydroxyphenyl)-propionic acid for example,
  N,N'-di-(3,5-di-tert.butyl-4-hydroxyphenylpropionyl)-hexamethylenediamine
  N,N'-di-(3,5-di-tert.butyl-4-hydroxyphenylpropionyl)-trimethylenediamine
  N,N'-di-(3,5-di-tert.butyl-4-hydroxyphenylpropionyl)-hydrazine 2. UV absorbers and light stabilizers 2.1. 2-(2'-Hydroxyphenyl)-benzotriazoles, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 4'-octoxy, 3',5'-di-tert.amyl-, 3',5'-bis-(α,α-dimethylbenzyl)-derivative.

2.2. 2-Hydroxy-benzophenones, for example, the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy derivative.

2.3. Esters of optionally substituted benzoic acids for example, phenyl salicylate, 4-tert.butyl-phenylsalicylate, octylphenyl salicylate, dibenzoylresorcinol, bis-(4-tert.butylbenzoyl)-resorcinol, benzoylresorcinol, 3,5-di-tert.butyl-4-hydroxybenzoic acid 2,4-di-tert.butyl-phenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate, bis-(1,2,2,6,6-pentamethylpiperidyl)-sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert.octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-dioctyloxyoxanilide, 2,2'-di-octyloxy-5,5'-di-tert.butyloxanilide, 2,2'-di-dodecyloxy-5,5'-di-tert.butyl-oxanilide, 2-ethoxy-2'-ethyl-oxanilide, N,N'-bis-(3-dimethylaminopropyl)-oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythrit diphosphite, tris-(2,4-di-tert.butylphenyl) phosphite, di-isodecylpentaerythritol diphosphite, di-(2,4-di-tert.butylphenyl)pentaerythritol diphosphite, tristearylsorbite triphosphite, tetrakis-(2,4-di-tert.butylphenyl)-4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythritol-tetrakis-(β-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxides, carbon black, graphite.

10. Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

The following examples illustrate the embodiments of this invention. In these examples, all parts given are by weight unless otherwise specified.

EXAMPLE I

1,1,1-Tris(3,5-di-tert-butyl-4-hydroxyphenylthio)methane

A solution of 19.0 g (80 mmol) of 3,5-di-tert-butyl-4-hydroxyphenylthiol in 4.0g (27 mmol) of triethylorthoformate is mixed with 10 drops of 6N HCl and the mixture heated to distill off resultant ethanol. The residue is recrystallized from ethanol to give 12.6 g (66%) of a white solid, mp. 217°–220° C.

Anal. Calcd. for $C_{43}H_{64}O_3S_3$: C, 71.2; H, 8.9. Found: C, 71.4; H, 9.2.

EXAMPLE II

1,1,1-Tris(3-tert-butyl-5-methyl-4-hydroxyphenylthio)methane

The procedure of Example 1 is followed using 30.0 g (0.15 mol) of 3-tert-butyl-5-methyl-4-hydroxyphenylthiol, 7.4 g (0.05 mol) of triethylorthoformate and 10 drops of 6N HCl. After 5 minutes of stirring at room temperature, the product crystallizes out of solution. The residue is recrystallized from toluene to give 29.3 g (98%) of a white solid, m.p. 171°–172° C.

Anal. Calcd. for $C_{34}H_{46}O_3S_3$: C, 68.2; H, 7.7. Found: C, 68.0; H, 7.7.

EXAMPLE III

1,1,1-Tris (2-methyl-5-tert-butyl-4-hydroxyphenylthio)methane

The procedure of Example 1 is followed using 5.0 g (25 mmol) of 2-methyl-5-tert-butyl-4-hydroxyphenylthiol, 1.28 g (8.5 mmol) of triethylorthoformate and 6 drops of 6N HCl. The residue is purified on Waters Prep. 500A HPLC using heptane/ethylacetate (70:30) as the eluent to give 1.71 g (34%) of a white solid, mp. 204–205° C.

Anal. Calcd. for $C_{34}H_{46}O_3S_3$: C, 68.2; H, 7.7. Found: C, 68.3; H, 8.1.

EXAMPLE IV

The procedure of Example 1 can also be utilized to prepare 1,1,1-tris(3,5-dimethyl-4-hydroxyphenylthio)methane with appropriate amounts of 3,5-dimethyl-4-hydroxyphenylthiol, triethylorthoformate and HCl, the product having a mpt. of 122°–125° C.

EXAMPLE V

Processing of Polypropylene

| Base Formulation | |
|---|---|
| Polypropylene* | 100 parts |
| Calcium Stearate | 0.10 parts |

*Profax 6501 from Himont U.S.A.

The stabilizers are solvent blended into polypropylene as solutions in methylene chloride and after removal of solvent by evaporation at reduced pressure, the resin is extruded using the following extruder conditions:

| | Temperature (°C.) |
|---|---|
| Cylinder #1 | 232 |
| Cylinder #2 | 246 |
| Cylinder #3 | 260 |
| Gate #1 | 260 |
| Gate #2 | 260 |
| Gate #3 | 260 |
| RPM | 100 |

The melt flow rate (MFR) is determined by ASTM method 1238 condition L. The melt flow rate is a measure of the molecular weight for a specific type of polymer. The results are shown below.

| | Melt Flow Rate (g/10 Min) After Extrusion | |
|---|---|---|
| Additive | 1 | 5 |
| Base Resin | 5.7 | 11.4 |
| 0.025% Compound of Example 1 | 2.8 | 4.5 |
| 0.050% Compound of Example 1 | 2.8 | 4.0 |
| 0.100% Compound of Example 1 | 2.7 | 3.7 |

These data illustrate that the instant compounds function as effective process stabilizers in polypropylene compositions.

EXAMPLE VI

Process Stability in Elastomers

The stabilizers are evaluated in an unstabilized cis-polybutadiene cement (Firestone Diene 35). After incorporation of stabilizers as cyclohexane solutions, the rubber is isolated by steam coagulation and the crumb is washed with water and dried under vacuum at 40° C. Samples for oven aging (70° C., circulating air oven) are prepared by pressing plaques (130 mils) at 100° C. for 1 minute. High temperature aging is carried out in a Brabender Plasticorder at 160° C. (60 RPM). The induction time to crosslinking (minutes to an increase in torque) is determined. The results are shown in the following table.

70° C. Oven Aging

| | | Gardner Color | |
|---|---|---|---|
| Additives | Days to Gel-15% | Init. | 35 Days |
| Base Elastomer | <7 | 1 | 7 |
| 0.25% Compound of Example 1 | >42 | 1 | 4 |

| | Brabender (160° C.) Time to Crosslink (Min) |
|---|---|
| Base Elastomer | 1.5 |
| 0.25% Compound of Example 1 | 30+ |

These data illustrate that the instant compounds function as effective antioxidants and process stabilizers in elastomers. They are also seen to prevent the discoloration of elastomers.

EXAMPLE VII

This example illustrates the stabilization of thick plaques (25 mil) of polypropylene by a compound of this invention. The testing procedure is as follows:

Unstabilized polypropylene powder (Hercules' Profax 6501) is thoroughly blended with the indicated amount of additive. The blended materials are then milled on a two roll mill at 182° C. for five minutes, after which time the stabilized polypropylene is sheeted from the mill and allowed to cool. The milled polypropylene is then cut into pieces and compression molded on a hydraulic press at 220° C. and 175 psi ($1.2 \times 10^6$ Pa) into 25 mil (0.635 mm) plaques. The sample is exposed to air in a forced draft oven at 150° C. The plaques are considered to have failed on showing the first signs of decomposition (e.g., cracking or brown edged).

| Additive compound of | Additive Concentration (% by weight) | Time to Failure (Hours) |
|---|---|---|
| Base Resin | — | <20 |
| Base Resin with 0.3% DSTDP | — | <20 |
| Example 1 | 0.2 | 100 |
| Example 1 with 0.3% DSTDP | 0.1 | 420 |

DSTDP - distearylthiodipropionate

EXAMPLE VIII

Unstabilized polypropylene powder (Hercules' Profax 6501) is thoroughly blended with the indicated amount of additive. The blended materials are then milled on a two roll mill at 182° C. for five minutes, after which time the stabilized polypropylene is sheeted from the mill and allowed to cool. The milled polypropylene is then cut into pieces and compression molded on a hydraulic press at 220° C. and 175 psi $1.2 \times 10^6$ Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

| Additive compound of | Additive Concentration (% by weight) | FS/BL Test Results (Hours to Failure) |
|---|---|---|
| None | — | 250 |
| Example 1 | 0.2 | 320 |

Summarizing, it is seen that this invention provides a group of compounds having improved stabilizing activity in a variety of organic materials. Variations may be made in proportions, procedures and materials without departing from the scope of the invention as defined by the following claims.

What is claimed is:

1. A compound of the formula

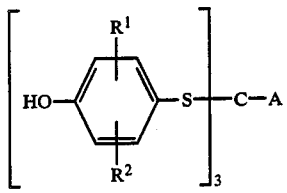

wherein $R^1$ and $R^2$ are independently hydrogen, alkyl of 1 to 18 carbon atoms, cycloalkyl of 5 to 12 carbon atoms, phenyl, phenyl substituted by alkyl of 1 to 18 carbon atoms, aralkyl of 7 to 9 carbon atoms or said aralkyl substituted by alkyl of 1 to 18 carbon atoms; and A is hydrogen, alkyl of 1 to 30 carbon atoms, cycloalkyl of 5 to 12 carbon atoms, aryl, aryl substituted by alkyl of 1 to 18 carbon atoms, aralkyl of 7 to 9 carbon atoms or said aralkyl substituted by alkyl of 1 to 12 carbon atoms.

2. The compound of claim 1, wherein $R^1$ and $R^2$ are in the ortho position to the hydroxyl group.

3. The compound of claim 2, wherein $R^1$ and $R^2$ are alkyl of from 1 to 8 carbon atoms.

4. The compound of claim 3, wherein $R^1$ is tert.butyl and $R^2$ is methyl or tert.butyl.

5. The compound of claim 4, wherein $R^1$ and $R^2$ are tert.butyl.

6. The compound of claim 1, wherein A is hydrogen, alkyl of 1 to 18 carbon atoms or phenyl.

7. 1,1,1-Tris (3,5-di-tert-butyl-4-hydroxyphenylthio)methane according to claim 4.

8. 1,1,1-Tris(3-tert-butyl-5-methyl-4-hydroxyphenylthio)methane according to claim 4.

9. 1,1,1-Tris(2-methyl-5-tert-butyl-4-hydroxyphenylthio)methane according to claim 1.

10. 1,1,1-Tris(3,5-dimethyl-4-hydroxyphenylthio)methane according to claim 1.

11. A composition of matter comprising an organic material subject to oxidative, thermal or actinic degradation stabilized with an effective stabilizing amount of a compound of claim 1.

12. The composition of claim 11, wherein the organic material is a synthetic polymer.

13. The composition of claim 12, wherein said polymer is selected from the group consisting of impact polystyrene, acrylonitrile/butadiene/sytrene, styrene/butadiene rubber, polyesters and poly-alpha-olefins.

14. A method for stabilizing an organic material against oxidative, thermal or actinic degradation which comprises incorporating into said organic material an effective stabilizing amount of a compound of claim 1.

* * * * *